(12) United States Patent
Sofka et al.

(10) Patent No.: US 8,605,969 B2
(45) Date of Patent: Dec. 10, 2013

(54) METHOD AND SYSTEM FOR MULTIPLE OBJECT DETECTION BY SEQUENTIAL MONTE CARLO AND HIERARCHICAL DETECTION NETWORK

(75) Inventors: Michal Sofka, Franklin Park, NJ (US); Jingdan Zhang, Plainsboro, NJ (US); Shaohua Kevin Zhou, Plainsboro, NJ (US); Dorin Comaniciu, Princeton Junction, NJ (US)

(73) Assignee: Siemens Corporation, Iselin, NJ (US)

( * ) Notice: Subject to any disclaimer, the term of this patent is extended or adjusted under 35 U.S.C. 154(b) by 432 days.

(21) Appl. No.: 13/080,964

(22) Filed: Apr. 6, 2011

(65) Prior Publication Data
US 2011/0243386 A1 Oct. 6, 2011

Related U.S. Application Data

(60) Provisional application No. 61/321,224, filed on Apr. 6, 2010, provisional application No. 61/424,710, filed on Dec. 20, 2010.

(51) Int. Cl.
*G06K 9/00* (2006.01)
(52) U.S. Cl.
USPC .......................................... 382/128; 382/181

(58) Field of Classification Search
USPC .................................................. 382/128, 181
See application file for complete search history.

(56) References Cited

U.S. PATENT DOCUMENTS

| | | | |
|---|---|---|---|
| 6,324,532 B1 * | 11/2001 | Spence et al. | 706/27 |
| 6,901,167 B2 | 5/2005 | Herley | |
| 7,286,707 B2 | 10/2007 | Liu et al. | |
| 7,702,596 B2 | 4/2010 | Tu et al. | |
| 7,848,566 B2 * | 12/2010 | Schneiderman | 382/159 |
| 8,092,388 B2 * | 1/2012 | Park et al. | 600/450 |
| 2002/0146173 A1 | 10/2002 | Herley | |
| 2008/0025588 A1 | 1/2008 | Zhang et al. | |
| 2008/0240532 A1 | 10/2008 | Carneiro et al. | |
| 2008/0292153 A1 * | 11/2008 | Binnig et al. | 382/128 |
| 2009/0304251 A1 | 12/2009 | Zheng et al. | |
| 2010/0119137 A1 | 5/2010 | Schwing et al. | |

* cited by examiner

*Primary Examiner* — Tom Y Lu

(57) ABSTRACT

A method and system for detecting multiple objects in an image is disclosed. A plurality of objects in an image is sequentially detected in an order specified by a trained hierarchical detection network. In the training of the hierarchical detection network, the order for object detection is automatically determined. The detection of each object in the image is performed by obtaining a plurality of sample poses for the object from a proposal distribution, weighting each of the plurality of sample poses based on an importance ratio, and estimating a posterior distribution for the object based on the weighted sample poses.

34 Claims, 15 Drawing Sheets

METHOD AND SYSTEM FOR MULTIPLE OBJECT DETECTION BY SEQUENTIAL MONTE CARLO AND HIERARCHICAL DETECTION NETWORK

This application claims the benefit of U.S. Provisional Application No. 61/321,224, filed Apr. 6, 2010 and U.S. Provisional Application No. 61/424,710, filed Dec. 20, 2010, the disclosures of which are herein incorporated by reference.

BACKGROUND OF THE INVENTION

The present invention relates to object detection in medical images, and more particularly, to multiple object detection using sequential Monte Carlo and a hierarchical detection network.

Multiple Object Detection has many applications in computer vision systems, for example in visual tracking, to initialize segmentation, or in medical imaging. For example, in medical imaging, multiple anatomic objects having a spatial relationship with each other can be detected. State of the art approaches for multi-object detection typically rely on an individual detector for each object class followed by post-processing to prune spurious detections within and between classes. Detecting multiple objects jointly rather than individually has the advantage that the spatial relationships between the objects can be exploited. However, obtaining a joint model of multiple objects is difficult in most practical situations.

BRIEF SUMMARY OF THE INVENTION

The present invention provides a method and system for multiple object detection in medical images. Embodiments of the present invention utilize sequential Monte Carlo estimation to sequentially detect multiple objects. Embodiments of the present invention use the relative locations of the objects to provide constraints to focus the search for each object in regions where the object is expected based on the locations of the other objects. Embodiments of the present invention automatically select the optimal order for object detection.

In one embodiment of the present invention, a plurality of objects are sequentially detected in an image in an order specified by a trained hierarchical detection network. The detection of each object in the image is performed by obtaining a plurality of sample poses for the object from a proposal distribution of object poses for the object, weighting each of the plurality of sample poses based on an importance ratio calculated for each sample pose, and estimating a posterior distribution for the object based on the weighted sample poses.

In another embodiment of the present invention, a hierarchical decision network for detecting multiple objects in an image is trained. A plurality of object detectors, each corresponding to one of the plurality of objects, are individually trained using a first set of annotated training data. A detection order for detecting the plurality of objects is automatically determined using a second set of annotated training data and the trained object detectors.

These and other advantages of the invention will be apparent to those of ordinary skill in the art by reference to the following detailed description and the accompanying drawings.

DETAILED DESCRIPTION

Figure 1:
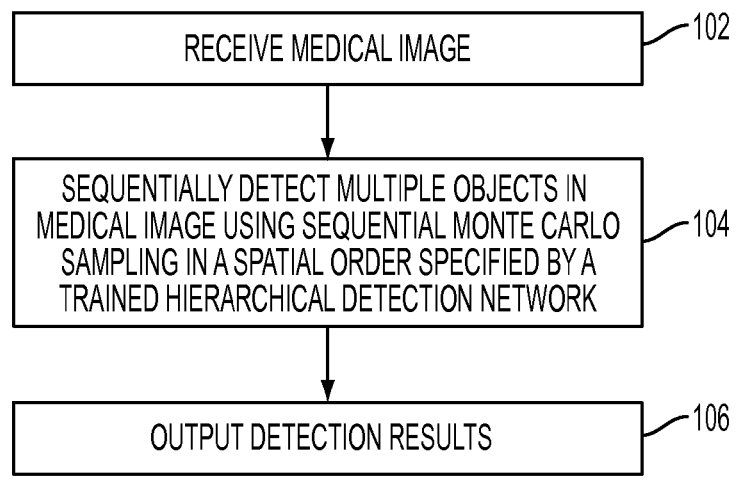
FIG. 1 illustrates a method for detecting multiple objects in a medical image according to an embodiment of the present invention.

The present invention relates to multiple object detection in medical images. Embodiments of the present invention are described herein to give a visual understanding of various organ classification methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Embodiments of the present invention may be applied to different imaging modalities, including but not limited to ultrasound, computed tomography (CT), magnetic resonance imaging (MRI), etc.

Since obtaining a joint model of multiple objects is difficult in many practical situations, the multi-object detection task can be solved using multiple individual object detectors connected by a spatial model. Relative locations of the objects provide constraints that help to make the system more robust by focusing the search for each object in regions where the object is expected based on locations of the other objects. Challenging aspects of such algorithms is designing detectors that are fast and robust, modeling the relationships between the objects, and determining the detection order. Embodiments of the present invention provide a method and apparatus for multiple object detection that address the above described challenges.

The computational speed and robustness of the multiple object detection method described herein can be increased by hierarchical detection. In multiple object detection, one problem is how to effectively propagate object candidates across levels of the hierarchy. This typically involves defining a search range at a fine level where the candidates from the coarse level are refined. Incorrect selection of the search range leads to higher computational speeds, lower accuracy, or drift of the coarse candidates towards incorrect refinements. The search range in embodiments of the present invention is part of the model that is learned from the training data. The performance of the multi-object detection method can be further improved by starting from objects that are easier to detect and constraining the detection of other objects by exploiting the object configurations. The difficulty of this strategy is selecting the order of detections such that the overall performance is maximized. In embodiments of the present invention, the detection schedule is designed to minimize the uncertainty of detections. Using the same algorithm used to optimize the order of object detections, the optimal schedule of hierarchical scales for detecting objects can also be obtained.

Embodiments of the present invention utilize sequential estimation techniques that are frequently applied to visual tracking. In visual tracking, the goal is to estimate, at time t, the object state $x_t$ (e.g., location and size) using observations $y_{0:t}$ (object appearance in video frames). This computation requires a likelihood of a hypothesized state that gives rise to observations and a transition model that describes the way states are propagated between frames. Since the likelihood models in practical situations lead to intractable inference, approximation by Monte Carlo methods, also known as particle filtering, have been widely adopted. At each time step t, the estimation involves sampling from the proposal distribution $p(x_t|x_{0:t-1}, y_{0:t})$ of the current state $x_t$ conditioned on the history of states $x_{0:t-1}$ up to time t−1 and the history of observations $y_{0:t}$ up to time t.

Embodiments of the present invention use the sequential Monte Carlo technique in multi-object detection. The multiple object detection method described herein samples from a sequence of probability distributions, but the sequence specifies a spatial order rather than a time order. The posterior distribution of each object pose (state) is estimated based on all observations so far. The observations are features computed from image neighborhoods surrounding the objects. The likelihood of a hypothesized state that gives rise to observations is based on a deterministic model learned using a large database of annotated images. The transition model that describes the way poses of objects are related is a Gaussian distribution.

Other object detection algorithms have typically focused on a fixed set of object pose parameters that are tested in a binary classification system. In embodiments of the present invention, employing the sequential sampling allows for the use of fewer samples of the object pose. This saves computational time and increases accuracy since the samples are taken from regions of high probability of the posterior distribution. Unlike in tracking, where the sequential order is naturally determined by time progression, the order in multi-object detection must be selected. In embodiments of the present invention, the order is selected such that the uncertainty of the detections is minimized. Accordingly, instead of using the immediate pre-cursor in the Markov process, the transition model can be based on any precursor, which is optimally selected. This leads to a Hierarchical Detection Network (HDN), which is explained in greater detail below. The likelihood of a hypothesized posed is calculated using a trained detector. The detection scale is introduced as another parameter of the likelihood model and the hierarchical schedule is determined in the same way as the spatial schedule.

FIG. 1 illustrates a method for detecting multiple objects in a medical image according to an embodiment of the present invention. As illustrated in FIG. 1, at step 102, a medical image is received. The medical image can be an image obtained using any imaging modality, including but not limited to, ultrasound, MRI, and CT. The image may be a 2D image or a 3D image volume. The medical image can be received directly from an image acquisition device, such as an ultrasound device, an MR scanner, or a CT scanner. It is also possible that the medical image is received by loading a medical image previously stored, for example, on a storage or memory of a computer system being used to implement the multiple object detection method.

At step 104, multiple objects are sequentially detected in the medical image using sequential Monte Carlo sampling in a spatial order specified by a trained hierarchical detection network. The hierarchical detection network is trained based on annotated ground truth training data to automatically select an order of object detection and a spatial hierarchy for the object detection. Sequential Monte Carlo sampling is used to detect the objects in the order specified by the hierarchical detection network, resulting in an estimated pose (location, orientation, and scale) of each of the objects in the medical image. At step 106, the detection results for the multiple objects are output. For example, the detection results can be output by displaying the detected objects in the medical image. It is also possible that the detection results can be output by storing the detection results, for example on a memory or storage of a computer system or on a computer readable medium.

Figure 2:
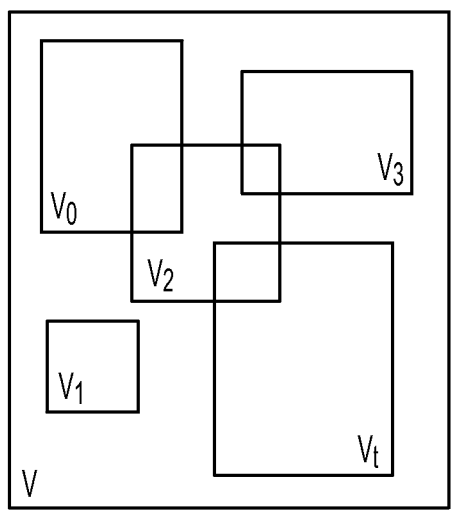
FIG. 2 illustrates a sequence of observations in a volume.

As described above, at step 104 of the method of FIG. 1, multiple objects are detected in an image using sequential Monte Carlo sampling. The state (pose) of a modeled object t is denoted as $\theta_t$ and the sequence of multiple object detections is denoted as $\theta_{0:t}=\{\theta_0, \theta_1, \ldots, \theta_t\}$. As used herein, $\theta_t=\{p, r, s\}$ denotes the position p, orientation r, and size s of the object t in the image. The set of observations for object t are obtained from the image neighborhood $V_t$. The neighborhood $V_t$ is specified by the coordinates of a bounding box within a d-dimensional image V, $V:R^d \to [0, 1]$. The sequence of observations is denoted as $V_{0:t}=\{V_0, V_1, \ldots, V_t\}$. This is possible since there exists prior knowledge for determining image neighborhoods $V_0, V_1, \ldots, V_t$. The image neighborhoods in the sequence $V_{0:t}$ may overlap and can have different size. An image neighborhood $V_i$ may even be the entire volume V. FIG. 2 illustrates a sequence of observations $V_0, V_1, \ldots, V_t$ in a volume V. As shown in FIG. 2, the set of observations $V_0, V_1, \ldots, V_t$ is a sequence of image patches. This sequence specifies a spatial order within an image, rather than a time order that is typically exploited in tracking applications.

The observations $V_t$ with a marginal distribution $f(V_t|\theta_t)$ describe the appearance of each object are assumed to be conditionally independent given the state $\theta_t$. The state dynamics, i.e., the relationships between the poses of the different objects, are modeled with an initial distribution $f(\theta_0)$ and a transition distribution $f(\theta_t|\theta_{0:t-1})$. It can be noted that embodiments of the present invention do not use the Markov transition $f(\theta_t|\theta_{t-1})$, as used in tracking applications.

The multi-object detection step (step 104 of FIG. 1) is performed by recursively applying prediction and update steps to obtain the posterior distribution $f(\theta_{0:t-1}|V_{0:t-1})$. The prediction step computes the probability density of the state of the object t using the state of the previous object t−1 and previous observations of all objects up to t−1:

$$f(\theta_{0:t}|V_{0:t-1}) = f(\theta_t|\theta_{0:t-1})f(\theta_{0:t-1}|V_{0:t-1}). \tag{1}$$

When detecting the object t, the observation $V_t$ is used to compute the estimate during the update step as:

$$f(\theta_{0:t}|V_{0:t}) = \frac{f(V_t|\theta_t)f(\theta_{0:t}|V_{0:t-1})}{f(V_t|V_{0:t-1})}, \tag{2}$$

where $f(V_t|V_{0:t-1})$ is the normalizing constant.

As simple as the above expressions may seem, these expressions do not have an analytical solution in general. This problem is addressed by drawing m weighted samples $\{\theta_{0:t}^j, w_t^j\}_{j=1}^m$ from the distribution $f(\theta_{0:t}|V_{0:t})$, where $\{\theta_{0:t}^j\}_{j=1}^m$ is a realization of state $\theta_{0:t}$ with weight $w_t^j$.

In most practical situations, sampling directly from $f(\theta_{0:t}|V_{0:t})$ is not feasible. Accordingly, embodiments of the present invention utilize the ides of importance sampling to introduce a proposal distribution $p(\theta_{0:t}|V_{0:t})$ which includes the support of $f(\theta_{0:t}|V_{0:t})$.

In order for the samples to be proper, the weights are defined as:

$$\overline{w}_t^j = \frac{f(V_{0:t}|\theta_{0:t}^j)f(\theta_{0:t}^j)}{p(\theta_{0:t}^j|V_{0:t})} \tag{3}$$

$$w_t^j = \overline{w}_t^j \Big/ \sum_{i=1}^m \overline{w}_t^i.$$

Since the current states do not depend on observations from other objects, then:

$$p(\theta_{0:t}|V_{0:t}) = p(\theta_{0:t-1}|V_{0:t-1})p(\theta_t|\theta_{0:t-1}, V_{0:t}). \tag{4}$$

The states are calculated as:

$$f(\theta_{0:t}) = f(\theta_0) \prod_{j=1}^t f(\theta_j|\theta_{0:j-1}). \tag{5}$$

Substituting (4) and (5) into (3), results in:

$$\overline{w}_t^j = \frac{f(V_{0:t}|\theta_{0:t}^j)f(\theta_{0:t}^j)}{p(\theta_{0:t-1}^j|V_{0:t-1})p(\theta_t^j|\theta_{0:t-1}^j, V_{0:t})} \tag{6}$$

$$= \overline{w}_{t-1}^j \frac{f(V_{0:t}|\theta_{0:t}^j)f(\theta_{0:t}^j)}{f(V_{0:t-1}|\theta_{0:t-1}^j)f(\theta_{0:t-1}^j)p(\theta_t^j|\theta_{0:t-1}^j, V_{0:t})} \tag{7}$$

$$= \overline{w}_{t-1}^j \frac{f(V_t|\theta_t^j)f(\theta_t^j|\theta_{0:t-1}^j)}{p(\theta_t^j|\theta_{0:t-1}^j, V_{0:t})}. \tag{8}$$

Embodiments of the present invention utilize the transition prior $f(\theta_t^j|\theta_{0:t-1}^j)$ as the proposal distribution. Hence, the importance weights can be calculated as:

$$\tilde{w}_t^j = \tilde{w}_{t-1}^j f(V_t|\theta_t^j). \tag{9}$$

It is to be understood that the present invention is not limited to the above proposal distribution, and more sophisticated proposal distributions can be designed to leverage relations between multiple objects during detection.

Figure 3:
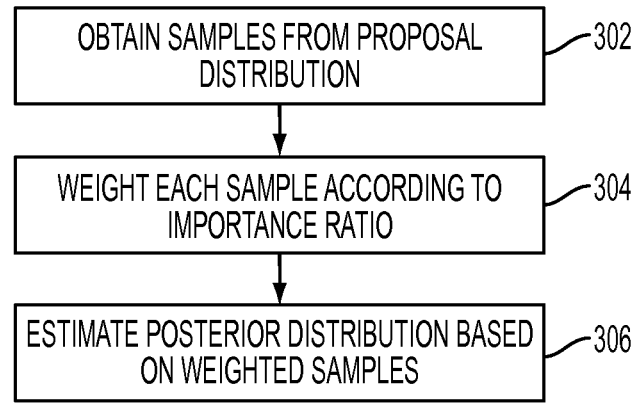
FIG. 3 illustrates a method of detecting an object using sequential sampling according to an embodiment of the present invention.

When detecting each object, the sequential sampling produces an approximation of the posterior distribution $f(\theta_{0:t}|V_{0:t})$ using the samples from the detection of the previous object. FIG. 3 illustrates a method of detecting an object using sequential sampling according to an embodiment of the present invention. The method of FIG. 3 is repeated for each object in order to implement step 104 of FIG. 1. At step 302, m samples are obtained from the proposal distribution $\theta_t^j \sim p(\theta_t^j|\theta_{0:t-1}^j)$. That is, a plurality of sample poses for the object t are calculated based on the proposal distribution from samples of the previous objects. The proposal distribution for an object is a predicted distribution of object poses that is calculated based on at least one previous object. It is to be understood that, for the first object detected, the proposal distribution is not based on previous objects. The proposal distribution for the first object may include all possible poses within the image data or may be a distribution of poses of the first object learned from annotated training data.

According to an advantageous implementation, the transition kernel $f(\theta_t^j|\theta_{0:t-1}^j)$ is adopted as the proposal distribution. In tracking applications, a Markov process is typically assumed for the transition kernel $f(\theta_t^j|\theta_{0:t-1}^j) = f(\theta_t^j|\theta_{t-1}^j)$, as time proceeds. However, the Markov process is too restrictive for multiple object detection. In multiple object detection, the best transition kernel may stem from an object other than the immediate precursor, depending on the anatomical context. Accordingly, a pairwise dependency can be used, such that:

$$f(\theta_t|\theta_{0:t-1}) = f(\theta_t|\theta_j), j \in \{0, 1, \ldots, t-1\}. \tag{10}$$

Accordingly, the proposal distribution for an object being detected can be calculated from any precursor object, not just the immediate precursor. According to an advantageous implementation, $f(\theta_t|\theta_j)$ can be modeled as a Gaussian distribution estimated from the training data. The precursor j for each object is automatically selected in the training of the hierarchical detection network. This training is described in greater detail below.

At step 304, each sample pose for the object is weighted based on the importance ratio $$\tilde{w}_t^j = \tilde{w}_{t-1}^j f(V_t|\theta_t^j). \tag{11}$$

The importance weights can be normalized. A random variable can be defined, such that $y \in \{-1, +1\}$, where $y=+1$ indicates the presence of the object and $y=-1$ indicates the absence of the object. To leverage the power of a large annotated dataset, a trained discriminative classifier is used in the observation model:

$$f(V_t|\theta_t) = f(y_t=+1|\theta_t, V_t), \tag{12}$$

where $f(y_t=+1|\theta_t, V_t)$ is the posterior probability (determined by the trained classifier) of object presence at $\theta_t$ in $V_t$. The discriminative classifier is trained from the annotated training data. According to a possible implementation, the classifier can be a probabilistic boosting tree (PBT) classifier. An individual classifier (detector) is trained for each object to be detected.

At step 306, the posterior distribution is estimated for the object and all previously detected objects based on the weighted samples. In particular, the weighted samples are resampled using their importance to obtain the unweighted approximation of $f(\theta_{0:t}|V_{0:t})$:

$$f(\theta_{0:t} | V_{0:t}) \approx \sum_{j=1}^{m} w_t^j \delta(\theta_{0:t} - \theta_{0:t}^j), \quad (13)$$

where $\delta$ is the Dirac delta function. Accordingly, at the detection of each object, the posterior distribution estimated for the previous objects is updated. In particular, after each landmark detection, a certain number of samples having the strongest weight can be kept for the object, and the location (pose) of each object can be determined by averaging the strongest samples for each object. The method of FIG. 3 is repeated for all of the objects, in the predefined order detected during training. Once the method of FIG. 3 has been repeated for all of the objects, the final posterior distribution results in the most likely poses for all of the objects.

Figure 4:
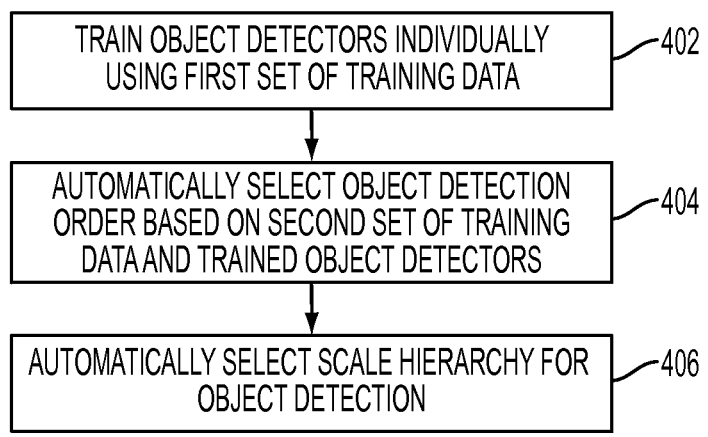
FIG. 4 illustrates a method of training a hierarchical detection network according to an embodiment of the present invention.

FIG. 4 illustrates a method of training a hierarchical detection network according to an embodiment of the present invention. The method of FIG. 4 utilizes training data annotated with ground truth poses for the objects to be detected. Unlike in a video, where the observations arise in a natural sequential fashion, the spatial order in multi-object detection must be selected. The goal is to select the order such that the posterior probability $P(\theta_{0:t}|V_{0:t})$ is maximized. Since determining this order has exponential complexity in the number of objects, a greedy approach is used. The training data can be split into two sets. As illustrated in FIG. 4, at step 402, the object detectors (classifiers) for the objects are trained individually using the first set of training data. The object detectors are trained to obtain posterior distributions $f(\theta_0, V_0)$, $f(\theta_1, V_1)$, ..., $f(\theta_t, V_t)$ of the respective objects based on features (observations) extracted from the image data. According to a possible implementation, each object detector can be a probabilistic boosting tree (PBT) classifier, but the present invention is not limited thereto.

Figure 5:
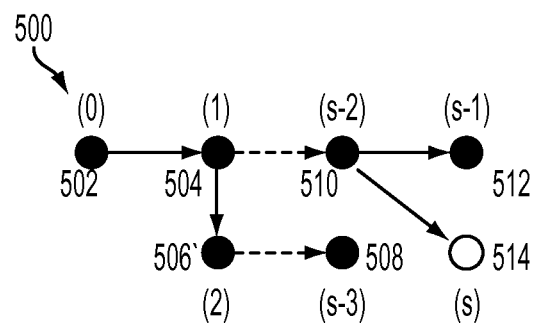
FIG. 5 illustrates detection order selection for a hierarchical detection network.

At step 404, the detection order is automatically selected based on the second set of training data and the trained object detectors. This step organizes the trained object detectors into a hierarchical detection network (HDN). FIG. 5 illustrates an HDN 500. The HDN is a pair-wise, feed-forward network. As shown in FIG. 5, each node 502, 504, 506, 508, 510, 512, and 514 of the HDN 500 represents a trained detector for a corresponding object (0), (1), (2), (s-3), (s-2), (s-1), and (s), respectively. The HDN is trained by recursively selecting the best remaining detector to add to the network. The first detector ((0) in FIG. 5) corresponds to the easiest object to detect correctly.

Referring to FIG. 5, suppose that the ordered detectors have been determined up to s-1, $\theta_0, \theta_1, \ldots, \theta_{s-1}$. The training method then must determine which object's (s) detector to add to the network and to which precursor object's (j) it should be connected. The method adds to the network the best pair [s,(j)] (or feed-forward path) that maximizes the expected value of the following score $S[s,(j)]$ over both s and (j) calculated from the second training set:

$$S[s, (j)] = \int_{\substack{\theta_s \in \Omega(\tilde{\theta}_s) \\ \theta_{(0:s-1)} \in \Omega(\tilde{\theta}_{(0:s-1)})}} f(\theta_{(0:s-1)} | V_{(0:s-1)}) f(\theta_s | \theta_{(j)}) f(V_s | \theta_s) d\theta_s d\theta_{(0:s-1)}, \quad (14)$$

where $\Omega(\tilde{\theta})$ is the neighborhood region around the ground truth $\tilde{\theta}$. The expected value is approximated as the sample mean of the cost computed for all examples of the second training set. In the HDN 500 of FIG. 5, the next detector was selected for object s with the precursor object (j) of (s-2).

Returning to FIG. 4, at step 406, the scale hierarchy for the object detection is automatically selected by adding a scale parameter to the HDN. Many previous object detection algorithms use a single size for image neighborhoods. Typically, this size and corresponding search step need to chosen a priori to balance the accuracy of the final detection result and computational speed. According to an advantageous embodiment of the present invention, this problem can be solved using hierarchical detection. During detection, larger object context is considered at coarser image resolutions resulting in robustness against noise, occlusions, and missing data. High detection accuracy is achieved by focusing the search in a smaller neighborhood at finer resolutions. Denoting the scale parameter as $\lambda$ in the HDN, the scale parameter $\lambda$ is treated as an extra parameter to $\theta_s$, and the order selection described in step 404 is used to select $\lambda$ as well. Accordingly, although in FIG. 4, steps 404 and 406 are shown as separate steps, one skilled in the art will understand that the order selection and scale selection can be performed simultaneously to generate a HDN that specifies the order and the scale for the detection of multiple objects.

In the embodiments described above, the multiple object detection method sequentially detects the objects in an order automatically determined in the training of the HDN. It is also possible that the detection order be set manually by a user or semi-automatically by a user manually setting a partial order and the remaining order being automatically determined.

The above described methodology for multiple object detection can be applied to detect various anatomical objects in various different imaging modalities. Various examples of multiple object detection using the above described methodology are described below.

Figure 6:
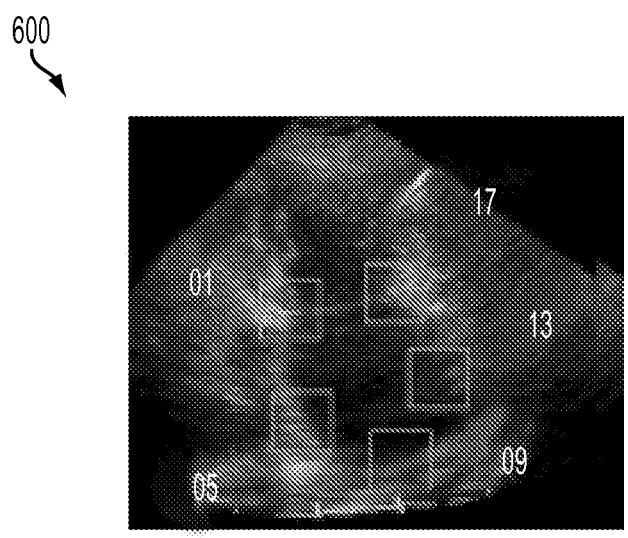
FIG. 6 illustrates five atrium landmarks of the left atrium in an A2C ultrasound image.

In one example, the multiple object detection method of FIGS. 1, 3, and 4 is used to detect five atrium landmarks of the left atrium (LA) in an apical two chamber (A2C) view of an ultrasound image. FIG. 6 illustrates the five atrium landmarks of the LA in an ASC ultrasound image 600. As shown in FIG. 6, the landmarks are numbered as 01, 05, 09, 13, and 17. The LA appearance is typically noisy since, during imaging, it is at the far end of the ultrasound probe. In this example, an expert annotated the five atrium landmarks in 417 training images. The size of the images is 120×120 pixels on average.

In an experiment to test different sampling strategies, three location detectors were trained independently using 281 training images. The detection order for this experiment was fixed as: 09→01→05 (see FIG. 6 for landmark numbering). Two different sampling strategies for object detection were tested within 136 unseen images. In the first sampling strategy (mean sampling), N number of samples are obtained with the strongest weight. In the second strategy (k-means sampling), up to M=2000 samples are obtained with the strongest weight and k-means clustering is performed to get N number of modes. After each landmark detection, these N samples are propagated to the next stage. The detected location is obtained by averaging the N samples for each landmark.

Figure 7:
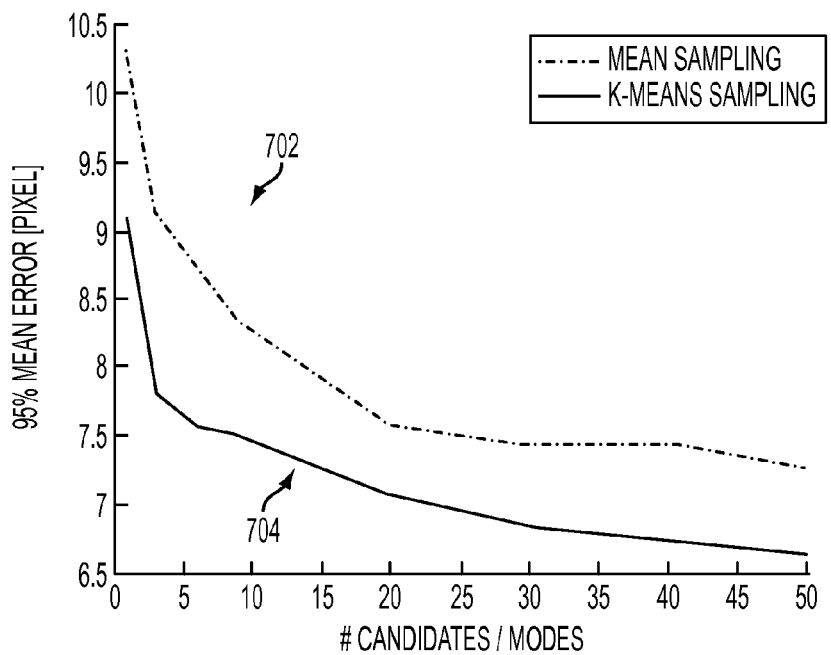
FIG. 7 illustrates a graph comparing the error for a mean sampling strategy and the k-means sampling strategy.

The number samples N was varied between 1 and 50. For each setting, the detection method was run to obtain the locations of the three landmarks. The mean of the 95% smallest errors was calculated by comparing the detected locations to manually labeled ground truths. FIG. 7 illustrates a graph comparing the error for the mean sampling strategy 702 and the k-means sampling strategy 704 over the number of samples (candidates or modes). As shown in FIG. 7, using the k-means sampling strategy 704, the errors are lower for all number of samples, as compared to the mean sampling strategy 702. Accordingly, by focusing the representation on the modes of the distribution using k-means sampling, a smaller number of samples can be used and the mean detection error is smaller.

In another experiment using the atrium landmarks illustrated in FIG. 6, the automatic selection of object detection order, as described above in connection with FIG. 4, was evaluated. The goal is to automatically determine the detection order of the five left atrium landmarks (01, 05, 09, 13, and 17) illustrated in FIG. 6. As in the previous experiment, the landmark detectors are trained using 281 annotated training images. A total of 46 annotated images from the data set were used to obtain the detection order. The remaining 90 images were used for detection and evaluation comparison.

Figure 8:
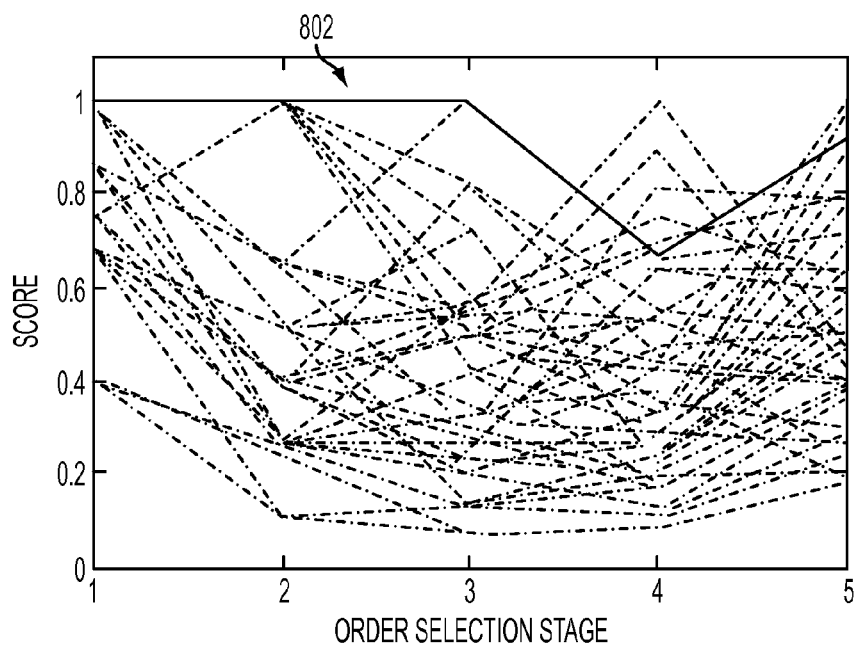
FIG. 8 illustrates a score value plotted for object detection stage for an automatically selected detection order and 100 random cases.

FIG. 8 illustrates the score value plotted for object detection stage for the automatically selected detection order and 100 random cases. The score values of FIG. 8 were normalized after each step. As shown in FIG. 8, line 802 represents the score value for the automatically determined detection order, and the other lines in the graph represent 100 randomly selected detection orders. As shown in FIG. 8, the automatically selected order 802 has high score values across all stages. The two randomly selected orders that have higher score values in the final stage have low score values at earlier stages. Accordingly, these detection orders were not selected by the automatic order selection method.

Figure 9:
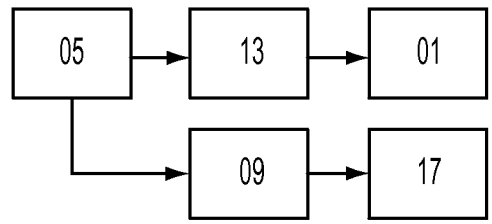
FIG. 9 illustrates hierarchical detection network generated by automatic object detection order selection for the atrium landmarks of FIG. 6.

As described above, the greedy order selection method selects the order with the highest score value at each step. FIG. 9 illustrates the HDN 900 generated by the automatic object detection order selection for the atrium landmarks of FIG. 6. As shown in the HDN 900 of FIG. 9, landmark 05 is detected first, and is the precursor for detecting landmarks 13 and 09. Landmark 13 is the precursor for detecting landmark 01, and landmark 09 is the precursor for detecting landmark 17.

Figure 10:
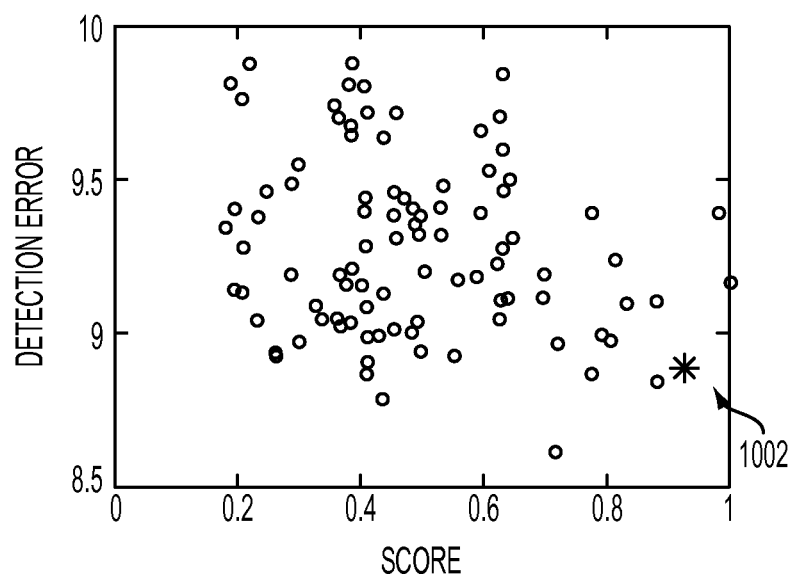
FIG. 10 illustrates a plot of the final detection error vs. the score calculated for the automatically selected object detection order and the 100 random orders.

The automatically selected sequential order (HDN 900) is further compared to the 100 randomly generated orders by calculating, for each order, the final detection error averaged over all testing images and detected landmarks, as well as calculating the score as the probability of states in the ground truth region (Equation 15) for the final selection stage normalized by the maximum probability across all stages. FIG. 10 illustrates a plot of the final detection error vs. the score calculated for the automatically selected object detection order and the 100 random orders. In FIG. 10, star 1002 represents the automatically selected order and the circles in the graph represent the 100 random orders. As shown in FIG. 10, the automatically selected order 1002 has a low mean error and a high probability (score), as compared to the 100 random orders. The order with the highest probability was not selected due to the greedy automatic selection strategy. This is because the probability of the states near ground truth was low for earlier objects in this detection order. Since in real detection scenarios, the ground truth is not available and sampling in low probability regions is not reliable, these sequential orders are not preferable to the automatically selected order.

Figure 11:
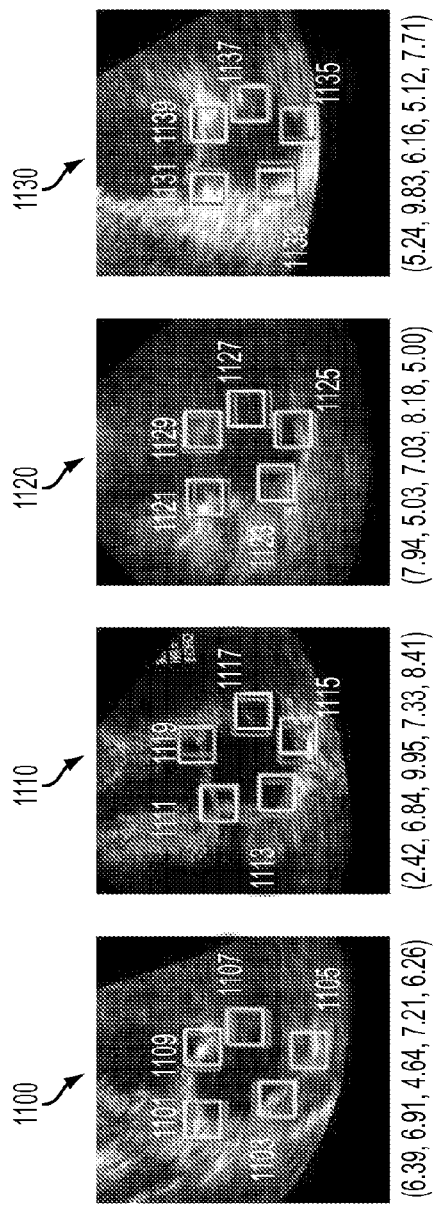
FIG. 11 illustrates detection results for detecting the five atrium landmarks in exemplary A2C ultrasound images.

FIG. 11 illustrates detection results for detecting the five atrium landmarks in exemplary A2C ultrasound images. The landmarks were detected using the sequential sampling in the order specified by the automatically selected HDN 900 of FIG. 9. As illustrated in FIG. 11, image 1100 shows detection results 1101, 1103, 1105, 1107, and 1109 for landmarks 01, 05, 09, 13, and 17, respectively. Image 1110 shows detection results 1111, 1113, 1115, 1117, and 1119 for landmarks 01, 05, 09, 13, and 17, respectively. Image 1120 shows detection results 1121, 1123, 1125, 1127, and 1129 for landmarks 01, 05, 09, 13, and 17, respectively. Image 1130 shows detection results 1131, 1133, 1135, 1137, and 1139 for landmarks 01, 05, 09, 13, and 17, respectively. The numbers below each of the images are the landmark detection errors (in pixels) for landmarks 01, 05, 09, 13, and 17, respectively, for each image.

In another exemplary implementation, the above described method for multiple object detection can be implemented to detect fetal brain structures in 3D ultrasound data. For example, the cerebellum, the cisterna magna, and the lateral ventricles can be detected in various planes of a 3D ultrasound volume. The output of the system is a visualization of the plane with the correct orientation and centering, as well as biometric measurement of the anatomy. In this example, 589 expert-annotated images were used for training and 295 for testing. The volumes have an average size of 250×200×150 mm. In this example, a HDN was trained that automatically selects detection order and scale for object detection.

Figure 12:
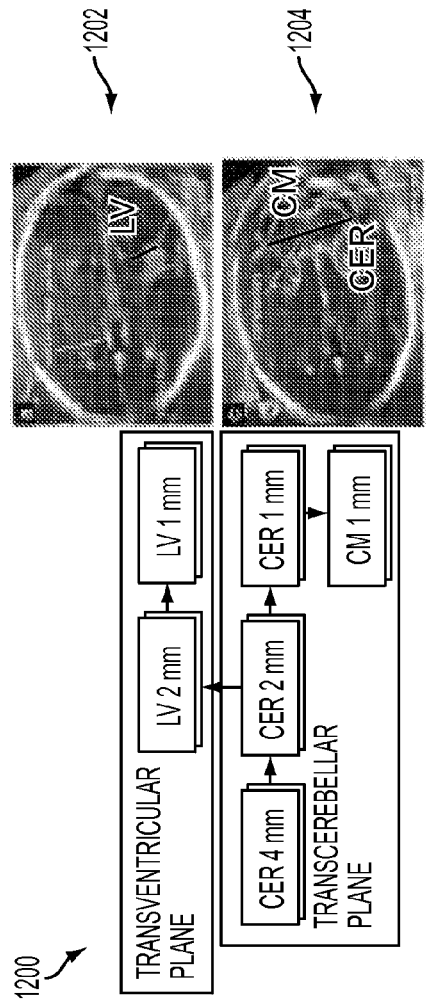
FIG. 12 illustrates a hierarchical detection network trained for fetal brain structure detection.

FIG. 12 illustrates an HDN trained for fetal brain structure detection. As shown in FIG. 12, the HDN 1200 specifies detection of the cerebellum (CER), the cisterna magna (CM), and the lateral ventricles (LV), and uses a hierarchy of three resolutions (4 mm, 2 mm, and 1 mm). In particular, HDN 1200 specifies that the cerebellum is first detected at a resolution of 4 mm in the transcerebellar plane. The 4 mm cerebellum detection is a precursor for detecting the cerebellum at 2 mm in the transcerebellar plane. The 2 mm cerebellum detection is a precursor for detecting the cerebellum at 1 mm in the transcerebellar plane. The 2 mm cerebellum detection is also a precursor for detecting the lateral ventricles at 2 mm in the transventricular plane. The 1 mm cerebellum detection is a precursor for detecting the cisterna magna at 1 mm in the transcerebellar plane. The 2 mm lateral ventricles detection is a precursor for detecting the lateral ventricles at 1 mm in the transventricular plane. Image 1202 shows an annotation of the lateral ventricles (LV) in the transventricular plane, and Image 1204 shows annotations of the cerebellum (CER) and the cisterna magna (CM) in the transcerebellar plane.

Figure 13:
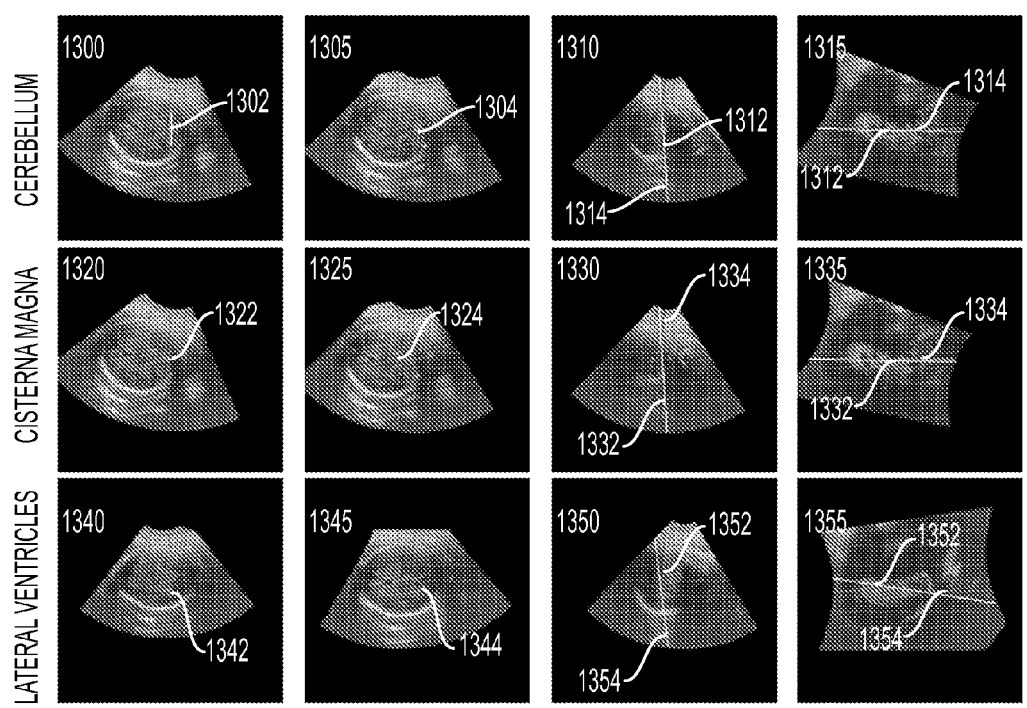
FIG. 13 illustrates exemplary detection results for the cerebellum, the cisterna magna, and the lateral ventricles in a 3D ultrasound.

Using the HDN 1200 of FIG. 12, the average detection error is 2.2 mm, which is lower than the average detection error 4.8 of a system without the HDN. FIG. 13 illustrates exemplary detection results for the cerebellum, the cisterna magna, and the lateral ventricles in a 3D ultrasound using the HDN 1200 of FIG. 12. As illustrated in FIG. 13, image 1300 shows the detected cerebellum 1302, image 1305 shows the ground truth cerebellum 1304, and images 1310 and 1315 are sagittal and coronal cross sections, respectively, showing the detection plane 1312 used to detect the cerebellum and the ground truth transcerebellar plane 1314. Image 1320 shows the detected cisterna magna 1322, image 1325 shows the ground truth cisterna magna 1324, and images 1330 and 1335 are sagittal and coronal cross sections, respectively, showing the detection plane 1332 used to detect the cisterna magna and the ground truth transcerebellar plane 1334. Image 1340 shows the detected lateral ventricles 1342, image 1345 shows the ground truth lateral ventricles 1344, and images 1350 and 1355 are sagittal and coronal cross sections, respectively, showing the detection plane 1352 used to detect the lateral ventricles and the ground truth transventricular plane 1354.

In another exemplary implementation, the above described method for multiple object detection can be implemented for detection of a fetal face in 3D ultrasound volumes. In this example, a total of 962 images were used in training and 48 testing. The gestational age of the fetus ranged from 21 to 40 weeks. The average size of the volumes is 157×154×104 mm. The major challenges of fetal face detection in 3D ultrasound data include varying appearance of structures due to different developmental stages and changes in the face region caused by movement of the extremities and the umbilical cord. The face was annotated by manually specifying mesh points on the face region. A bounding box of the mesh specifies the pose that is automatically detected using the multiple object detection method.

Figure 14:
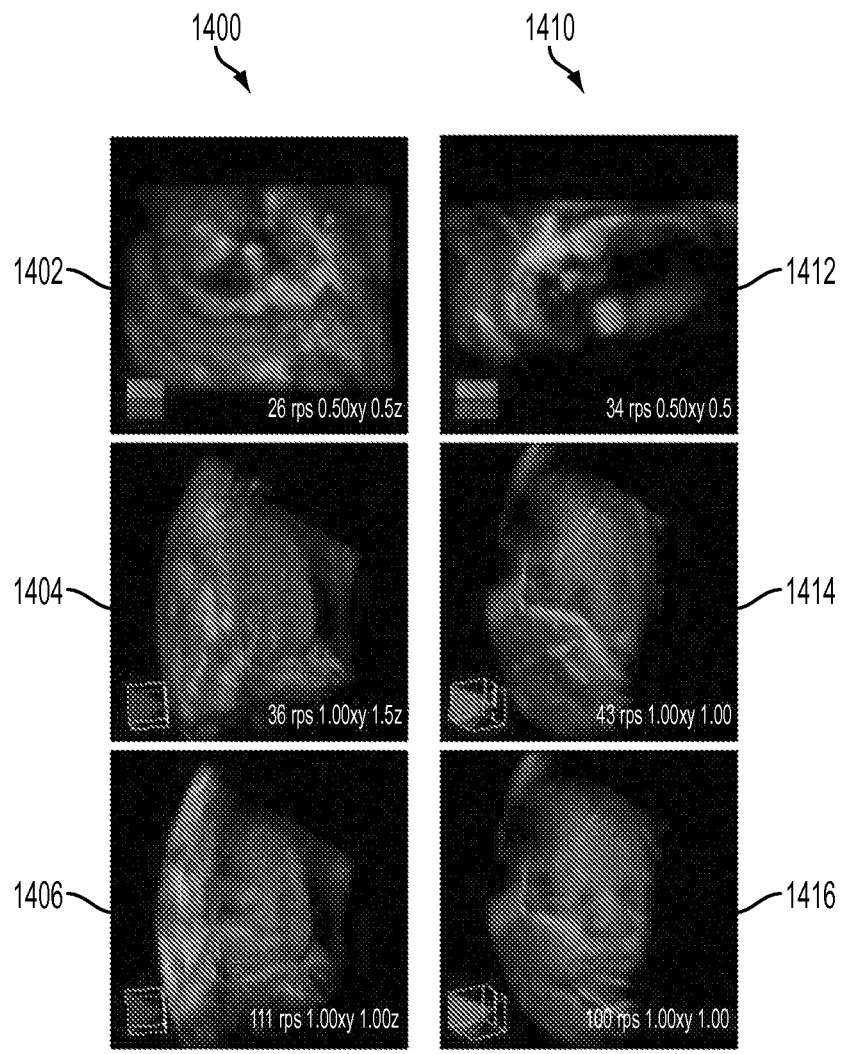
FIG. 14 illustrates exemplary detection results for fetal face detection in 3D ultrasound data

The HDN trained for the fetal face detection includes three hierarchical levels of facet detection, at resolutions of 4 mm, 2 mm, and 1 mm. The final training error was 5.48 mm and the testing error was 10.67 mm. FIG. 14 illustrates exemplary detection results for fetal face detection in 3D ultrasound data. As illustrated in FIG. 14, column 1400 shows fetal face detection results 1402, 1404, and 1406 for a first 3D ultrasound volume and column 1410 shows fetal face detection results 1412, 1414, and 1416 for a second 3D ultrasound volume. Images 1402 and 1410 show initial poses detected after loading the respective volumes. Images 1404 and 1414 show the fetal faces automatically detected at a finest resolution, and images 1406 and 1416 show the automatically detected fetal faces after volume carving of the region in front of the face.

Figure 15:
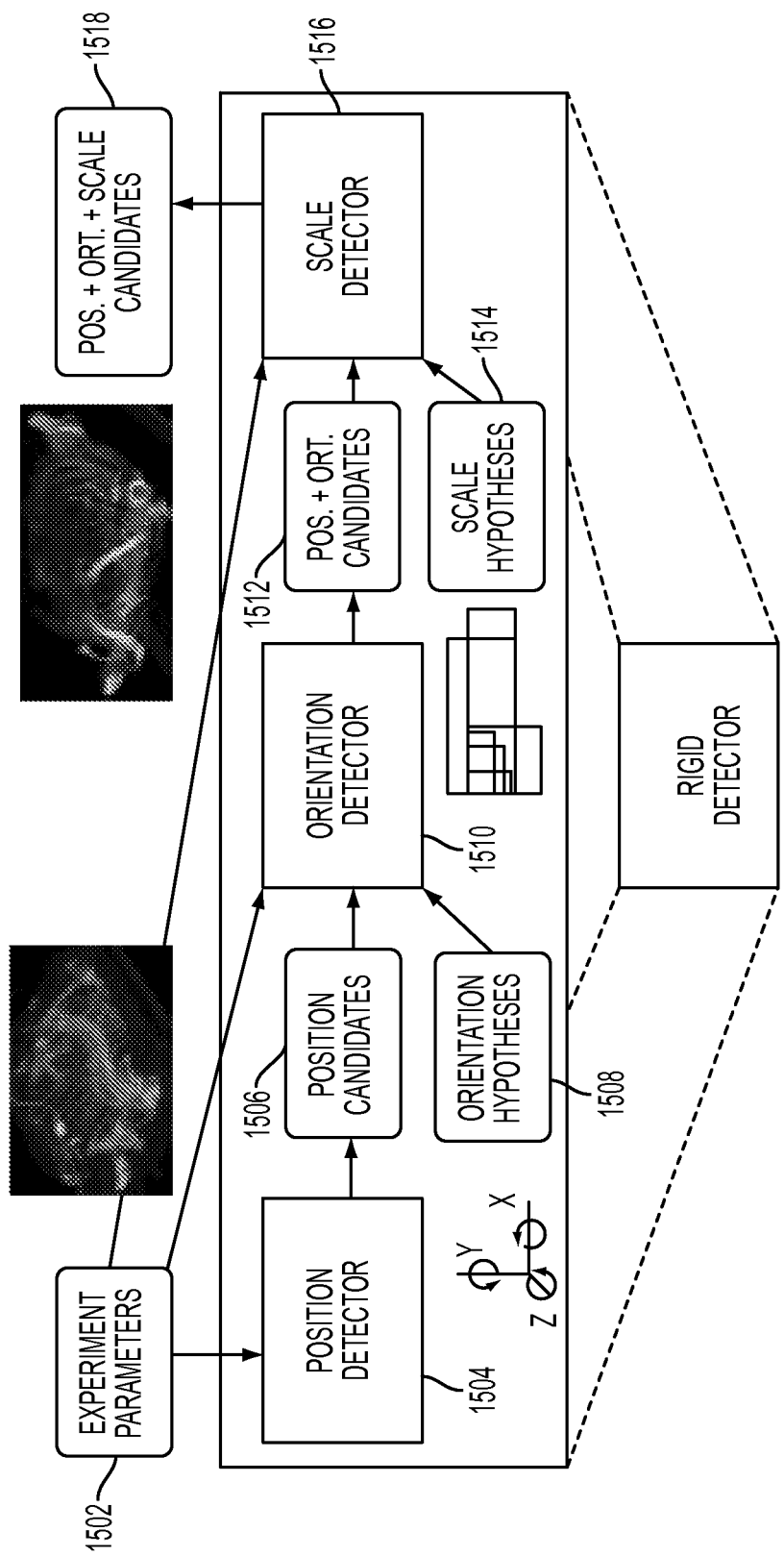
FIG. 15 illustrates a network that corresponds to a marginal space learning algorithm for estimating the pose of an object.

In another example described below, the method for multiple object detection is again used to detect brain structures in 3D ultrasound. In particular, in this example, the cerebellum and corpus callosum are detected in a 3D ultrasound volume. In detecting these brain structures, a rigid detectors using marginal space learning (MSL) are trained for the cerebellum and the corpus callosum. FIG. 15 illustrates a simple network that corresponds to the MSL algorithm for estimating the pose (9-dimensional similarity transform) of an object. This network is referred to herein as a rigid detector 1500. The object localization happens in three operations. Given an input image, specified in the experiment parameters 1502, the initial position estimate for the object is obtained from a trained position detector 1504. The output of this operation is the list of most probable position candidates 1506. The position candidates 1506, along with orientation hypotheses 1508 are input to a trained orientation detector 1510, which outputs most likely position and orientation candidates 1512 (6D pos.+ort. candidates). The position and orientation candidates 1512, along with scale hypotheses 1514, are input to a trained scale detector 1516, which outputs a list of most likely pose parameters (pos.+ort.+scale candidates) 1518.

The output of the cerebellum and corpus callosum detection is a visualization of the plane with correct orientation and centering of each structure. The structures are used in OB/GYN practice to assess fetus health and growth. Cerebellum pose can be determined using a hierarchy of rigid detectors. The detection hypotheses from a lower resolution image are propagated to the higher resolution image in both training and detection. The next detector is constrained to only search a region of interest defined by the union of neighborhood regions surrounding candidates with the highest probability. The structure at different resolutions is therefore treated as another object and the sampling of probability distributions for calculating the prediction and update steps follows Equations (1) and (2). This way, the search space at each resolution level is decreased, which results in higher efficiency and robustness.

Figure 16:
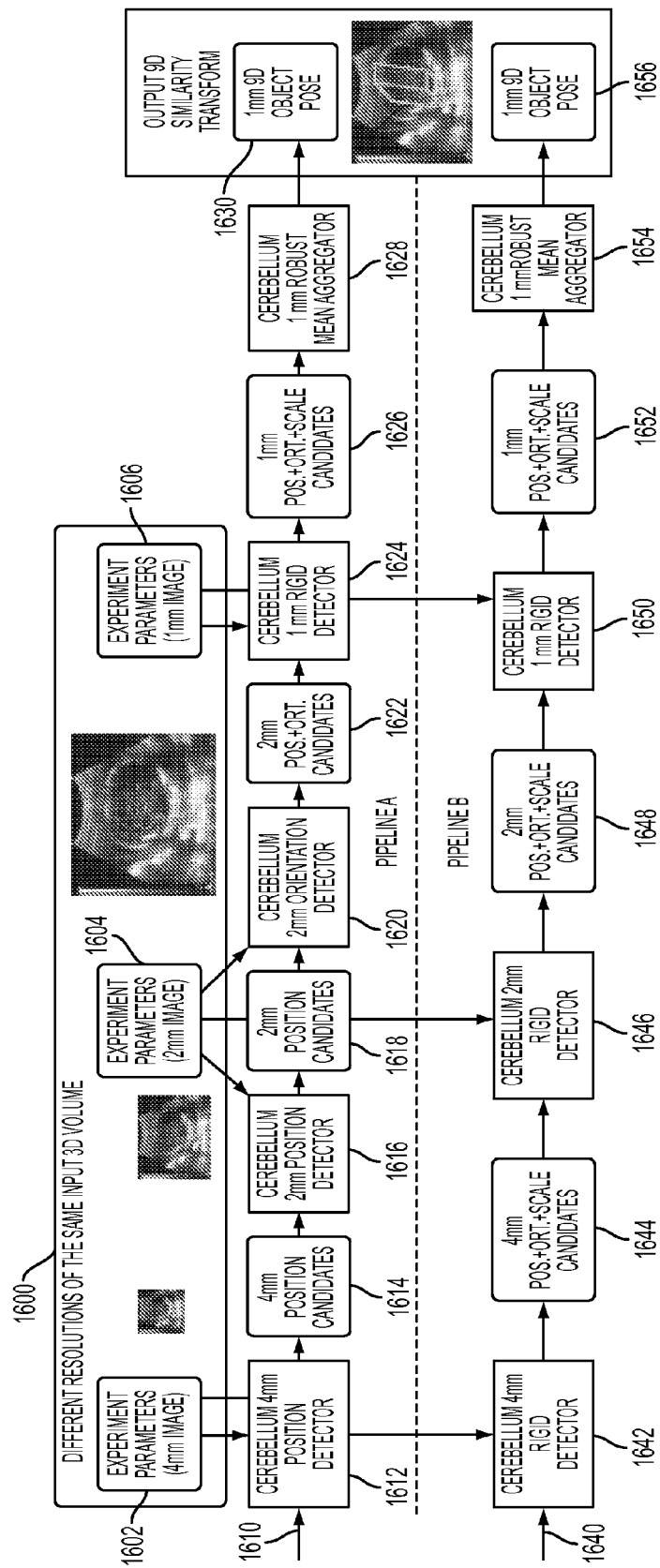
FIG. 16 illustrates two possible hierarchical detection networks for cerebellum detection.

FIG. 16 illustrates two possible hierarchical detection networks 1610 and 1640 for cerebellum detection. Both networks 1610 and 1640 utilize a hierarchy of detectors using an input image volume 1600 at resolutions of 4 mm (1602), 2 mm (1604), and 1 mm (1606). In pipeline A (network 1610), experiment parameters from the 4 mm volume 1602 are input to a 4 mm position detector 1612, which outputs 4 mm position candidates 1614. The 4 mm position candidates 1614 are input to a 2 mm position detector 1616 to constrain a search range of the 2 mm position detector 1616. Experiment parameters from the 2 mm volume 1604 are input to the 2 mm position detector 1616, which outputs 2 mm position candidates 1618. The 2 mm position candidates 1618, along with the experiment parameters from the 2 mm volume 1604, are input to a 2 mm orientation detector 1620, which outputs 2 mm position and orientation candidates 1622. The 2 mm position and orientation candidates 1622, along with experiment parameters from the 1 mm volume 1606, are input into a 1 mm rigid detector 1624, which outputs 1 mm pose (pos.+ort.+scale) candidates 1626. The 1 mm pose candidates 1626 are input to a robust mean aggregator 1628 that combines the pose candidates 1626 weighted by their probabilities to determine the final 9D similarity transform (object pose) 1630.

In pipeline B (network 1640), experiment parameters from the 4 mm volume 1602 are input to a 4 mm rigid detector 1642, which outputs 4 mm pose (pos.+ort.+scale) candidates 1644. The 4 mm pose candidates 1644, along with experiment parameters from the 2 mm volume 1604, are input to a 2 mm rigid detector 1646, which outputs 2 mm pose (pos.+ort.+scale) candidates 1648. The 2 mm pose candidates 1648, along with the experiment parameters from the 1 mm volume 1606, are input into a 1 mm rigid detector 1650, which outputs 1 mm pose (pos.+ort.+scale) candidates 1652. The 1 mm pose candidates 1652 are input to a robust mean aggregator 1654 that combines the pose candidates 1652 weighted by their probabilities to determine the final 9D similarity transform (object pose) 1656.

Figure 17:
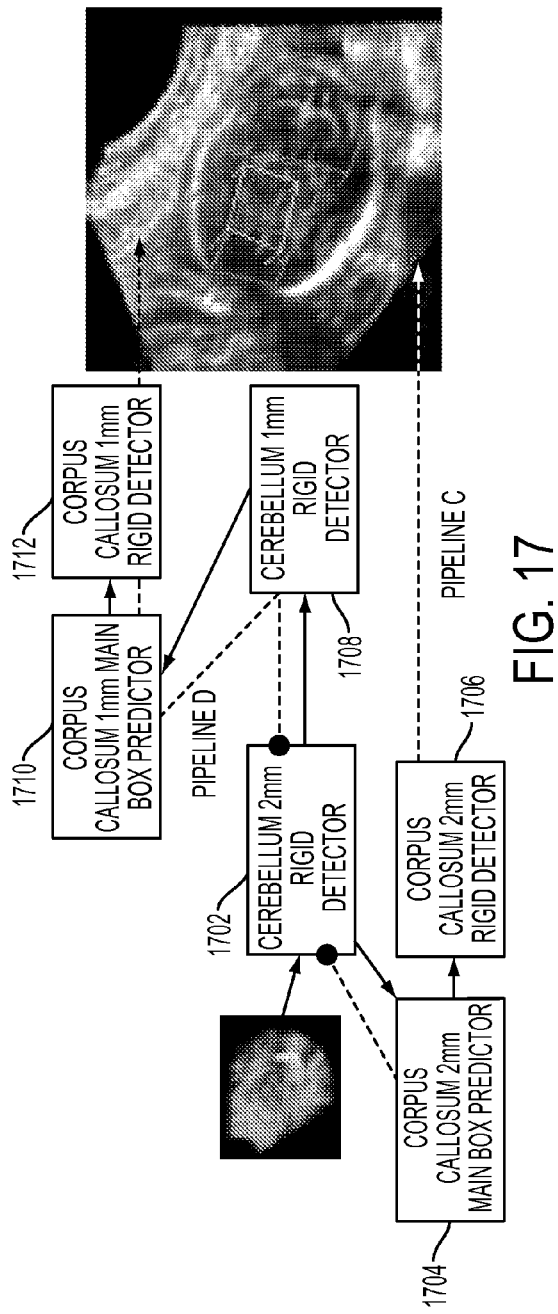
FIG. 17 illustrates two possible corpus callosum detection pipelines.

Once the cerebellum is detected (e.g., using pipeline A or pipeline B), the candidates with the highest probability are used to predict the pose parameters of the corpus callosum. This sampling and prediction is performed following Equation (1) and using the prediction kernel from Equation (10). The prediction kernel is Gaussian, and is implemented in a mean box predictor module. Using candidates with the highest probability, the corpus callosum detection continues using a rigid detector. FIG. 17 illustrates two possible corpus callosum detection pipelines (C and D). As illustrated in FIG. 17, both pipeline C and pipeline D start with a 2 mm rigid detector 1702. In pipeline C, candidate detections from the cerebellum at 2 mm are used by a 2 mm corpus callosum mean box predictor 1704 to predict pose parameters for the corpus callosum at 2 mm, which are input to a 2 mm corpus callosum rigid detector 1706. The 2 mm corpus callosum rigid detector 1706 detects the pose of the corpus callosum at 2 mm. In pipeline D, candidate detections from the cerebellum at 2 mm are input to a 1 mm cerebellum rigid detector 1708. The 1 mm cerebellum candidates are used by a 1 mm mean box predictor 1710 to predict pose parameters for the corpus callosum at 1 mm, which are input to a 1 mm corpus callosum rigid detector 1712. The 1 mm corpus callosum rigid detector 1712 detects the pose of the corpus callosum at 1 mm.

Figure 19:
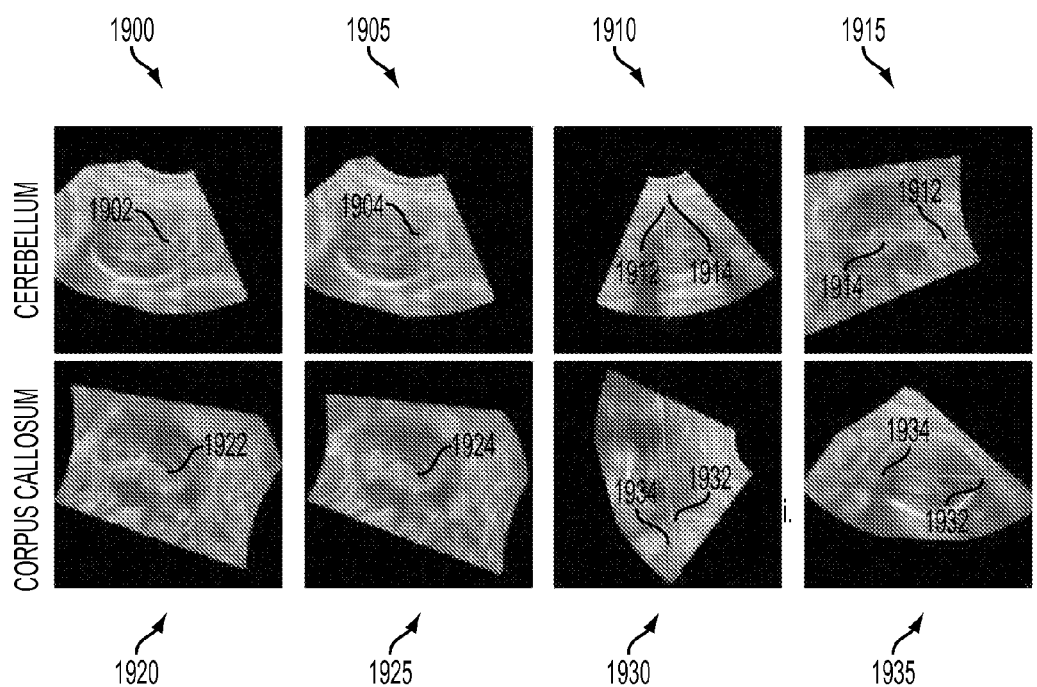
FIG. 19 illustrates detection results for the cerebellum and the corpus callosum in a 3D ultrasound volume.

The cerebellum detection networks in pipelines A and B of FIG. 16 were trained using 990 expert-annotated volumes. The volumes were annotated by marking a measurement line in the cerebellum plane (see FIG. 19). The cerebellum measurement is used in OB/GYN practice to assess fetus health and growth. The corpus callosum detection modules in pipelines C and D of FIG. 17 were trained using 636 volumes. Since these experiments were not concerned with the corpus callosum measurement, the annotation line was drawn from the bottom of the genu inside the body of the corpus callosum, as shown in FIG. 19. The annotation planes and lines define the pose of each structure. A total of 107 volumes were used for testing. The volumes have an average size of 250×200× 150 mm. The separation of the volumes into training and testing data sets was random, and the two datasets are disjoint.

Figure 18:
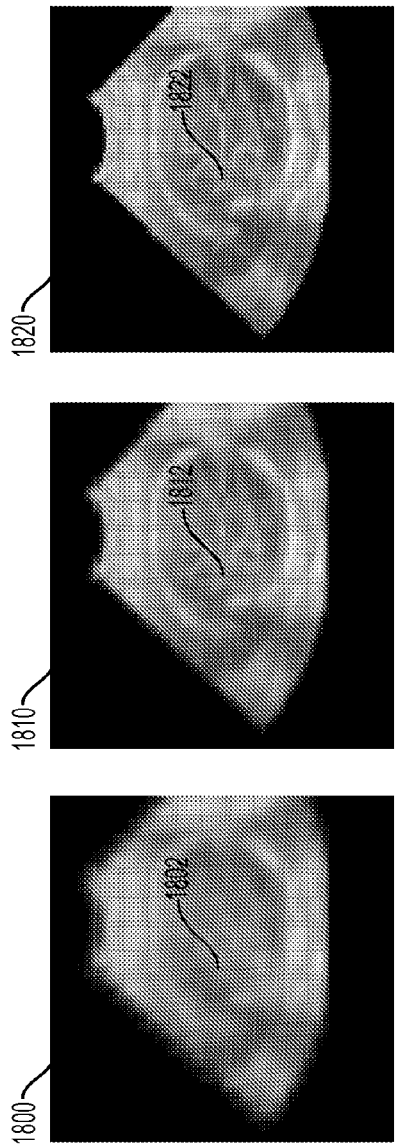
FIG. 18 illustrates cerebellum annotations at 4 mm, 2 mm, and 1 mm, resolutions.

Quantitative evaluation of the automatic cerebellum detection and measurement is in Table 1 below. As shown in Table 1, the median measurement error of pipeline A is 3.09 mm and the median measurement error of pipeline B is 3.38 mm. Accordingly, pipeline A provides more accurate measurements than pipeline B, despite the fact that the network for pipeline A is simpler (it uses only a position detector at 4 mm resolution and position and orientation detectors at 2 mm, as opposed to rigid detectors as in pipeline B). This is caused by an insufficient amount of detail at the 4 mm resolution to disambiguate the orientation of the fetus skull. FIG. 18 illustrates cerebellum annotations at 4 mm, 2 mm, and 1 mm resolutions. As shown in FIG. 18, image 1800 shows a cerebellum annotation line 1802 at 4 mm, image 1810 shows a cerebellum annotation line 1812 at 2 mm, and image 1820 shows a cerebellum annotation line 1822 at 1 mm. As shown in FIG. 18, the coarse 4 mm resolution volume 1800 has insufficient details causing ambiguity of the fetus skull orientation. The annotation line highlights the cerebellum, which is difficult to distinguish at 4 mm, but is much more clear at 2 mm and 1 mm resolutions.

TABLE 1

|  | Median | Med. Std. | Max. |
| --- | --- | --- | --- |
| Pipeline A | 3.09 | 1.71 | 7.45 |
| Pipeline B | 3.38 | 1.78 | 6.44 |

Quantitative evaluation of the automatic corpus callosum detection is in Table 2 below. The median measurement error of pipeline C is 4.83 mm and the median measurement error of pipeline D is 4.20 mm, respectively. The results at 1 mm resolution (pipeline D) are more accurate thanks to the more reliable cerebellum candidates at this resolution.

TABLE 2

|  | Median | Med. Std. | Max. |
| --- | --- | --- | --- |
| Pipeline C (2 mm) | 4.83 | 2.38 | 8.68 |
| Pipeline D (1 mm) | 4.20 | 2.13 | 9.91 |

FIG. 19 illustrates detection results for the cerebellum and the corpus callosum in a 3D ultrasound volume using pipelines A and D, respectively. As illustrated in FIG. 19, image 1900 shows the detected cerebellum 1902, image 1905 shows the ground truth cerebellum 1904, and images 1910 and 1915 are sagittal and coronal cross sections, respectively, showing the detected detection plane 1912 for the cerebellum and the ground truth detection plane 1914 for the cerebellum. Image 1920 shows the detected corpus callosum 1922, image 1925 shows the ground truth corpus callosum 1924, and images 1930 and 1935 are sagittal and coronal cross sections, respectively, showing the detected detection plane 1932 for the corpus callosum and the ground truth detection plane 1934 for the corpus callosum.

According to another embodiment, the above described multiple object detection method can be adapted to detect an object boundary in addition to the object pose. In one example, a liver boundary can be detected in a 3D MRI volume. Boundary detection occurs similarly to the hierarchical detection network, and first proceeds by detecting a shape in a learnt sub-space. Given a mean shape, $\hat{P} = \{\hat{p}_i \in \mathfrak{R}^3\}_{i=1}^n$, and few modes (e.g., 3) of shape variation, $U_j = \{u_i^j\}_{i=1}^n$ (obtained by procrustus analysis of training data), a new shape in the subspace can be synthesized as a linear combination of the modes:

$$p_i(\lambda_j, r, s, t) = T(r, s, t)\left(\hat{p}_i + \sum_j \lambda_j u_i^j\right), \quad (15)$$

where $T(r, s, t)$ is a similarity matrix defined by rotation r, scale s, and translation t. The parameters in the shape space, $\theta_{pca} = \{\lambda_1, \lambda_2, \lambda_3\}$, are estimated in the same way as an HDN using a discriminative classifier (Equation 12), and the transformation $(r, s, t)$ comes directly from estimating the pose of the desired structure, or through a prediction phase.

The second step of a free-form refinement of the mesh. In this phase, the mesh vertices themselves are the parameters $\theta$ to be estimated. The update $p_i \leftarrow p_i + \alpha_i n_i$ is calculated in the direction of the normal $n_i$. Again, $\alpha_i$ is obtained through the use of a trained discriminative model:

$$\alpha_i = \mathrm{argmin}_{-\tau \leq \alpha \leq \tau} f(y_i = +1 | V_{0:i}, p_i + \alpha n_i), \quad (16)$$

where $\tau$ is the search range along the normal. This update is interleaved with surface smoothing and updating the normal $n_i$. In practice, the mesh refinement is done on a three level mesh hierarchy, where $\hat{P}_2 \subset \hat{P}_1 \subset \hat{P}_0$, with the coarser levels being detected first.

The boundary detection algorithm naturally maps to concepts in an integrated detection network. A PCA detector takes as ins input a shape subspace and a single similarity transform (e.g., calculated by aggregating a set of candidates), which it augments with the detected PCA coefficients $\lambda_j$. A mesh synthesizer uses these candidates along with the shape subspace to generate an output mesh. Finally, a boundary detector accepts an input mesh and outputs the refined mesh. Internally, the boundary detector optionally upsamples the input mesh before performing detection.

Figure 20:
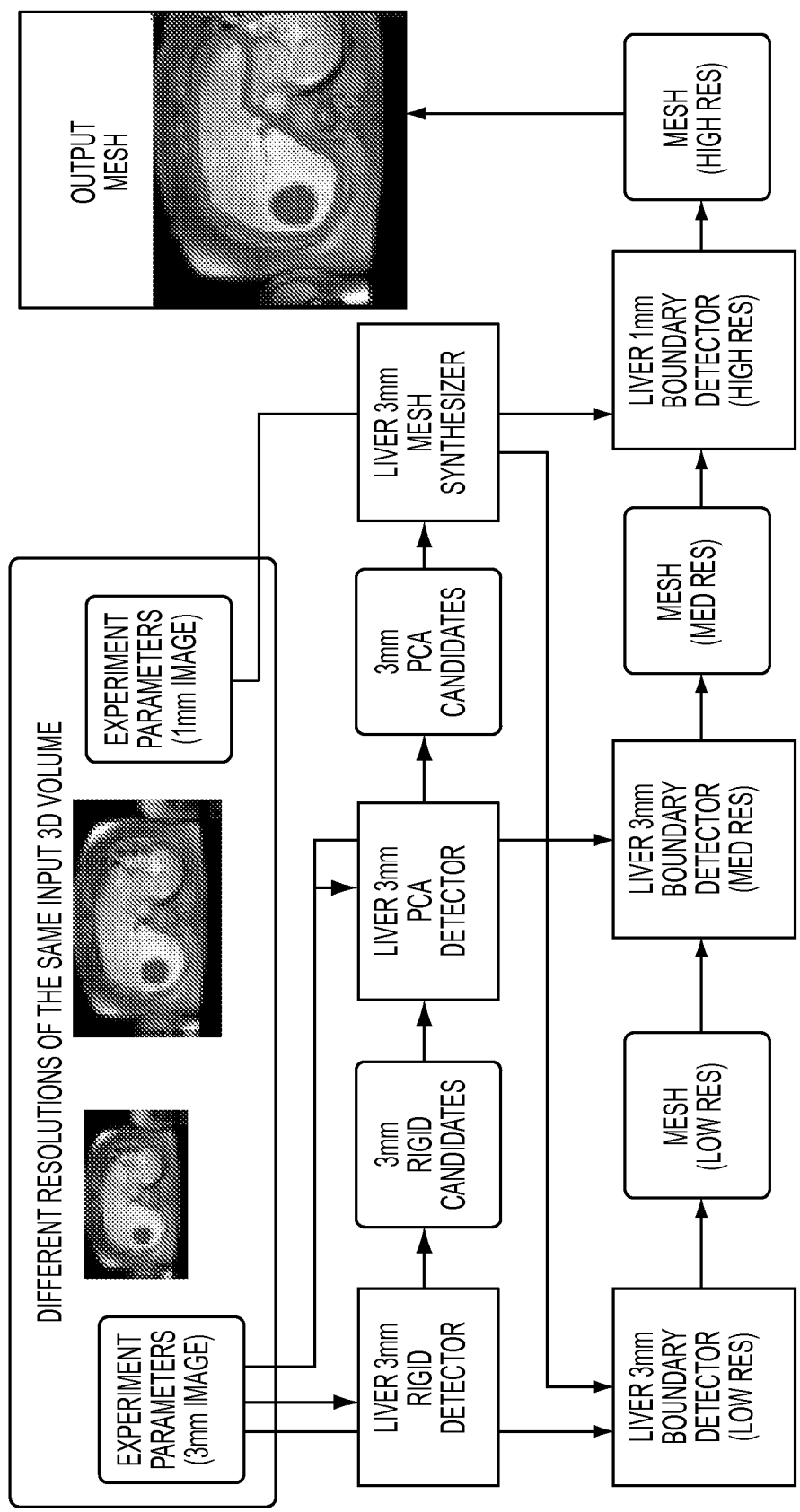
FIG. 20 illustrates a boundary detection network for detecting a liver boundary in a 3D MRI volume.

FIG. 20 illustrates a boundary detection (or segmentation) network for detecting a liver boundary in a 3D MRI volume. As shown in FIG. 20, rigid detection is used to initialize the boundary detection hierarchy, which is performed first on 3 mm data, then on 1 mm data. The mean liver mesh and shape subspace are built by performing procrustes analysis on manually annotated training examples. The mesh hierarchy includes a low resolution mesh with 602 vertices, a middle resolution with 1202 vertices, and the finest resolution at 2402 vertices. The low and middle resolution boundary detectors are trained on 3 mm data, whereas the high resolution is detected on 1 mm resolution volumes.

Figure 21:
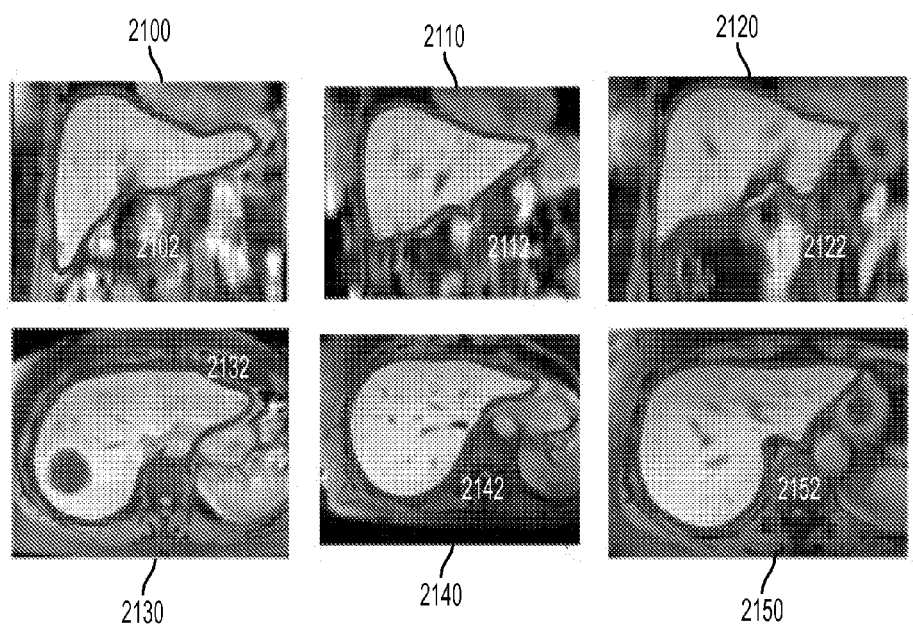
FIG. 21 illustrates exemplary liver boundary detection results in MRI slices.

The pipeline illustrated in FIG. 20 was trained on 59 annotated input volumes with dimensions as large as 420×300× 432 mm. Using 3-fold cross-validation, we compared the mesh-to-mesh distance of the detected results. Through an integrated detection network, it is possible to reconfigure the detection pipeline to remove the middle parts of the algorithm. Table 3, below, illustrates the accuracy after running several variations of the pipeline. As suggested by Table 3, the intermediate detection phases are necessary not only for performance, but also for accuracy. FIG. 21 illustrates exemplary liver boundary detection results in MRI slices. As shown in FIG. 21, images 2100, 2110, 2120, 2130, 2140, and 2150 show liver boundary detection results 2101, 2112, 2122, 2132, 2142, and 2152, respectively.

TABLE 3

| Method | Mean | Mean Std. | Median |
|---|---|---|---|
| Entire Pipeline | 2.53 | 1.82 | 1.81 |
| No 3 mm (med res.) | 3.72 | 2.17 | 3.28 |
| No (PCA or middle mesh) | 5.26 | 2.38 | 4.79 |

Figure 22:
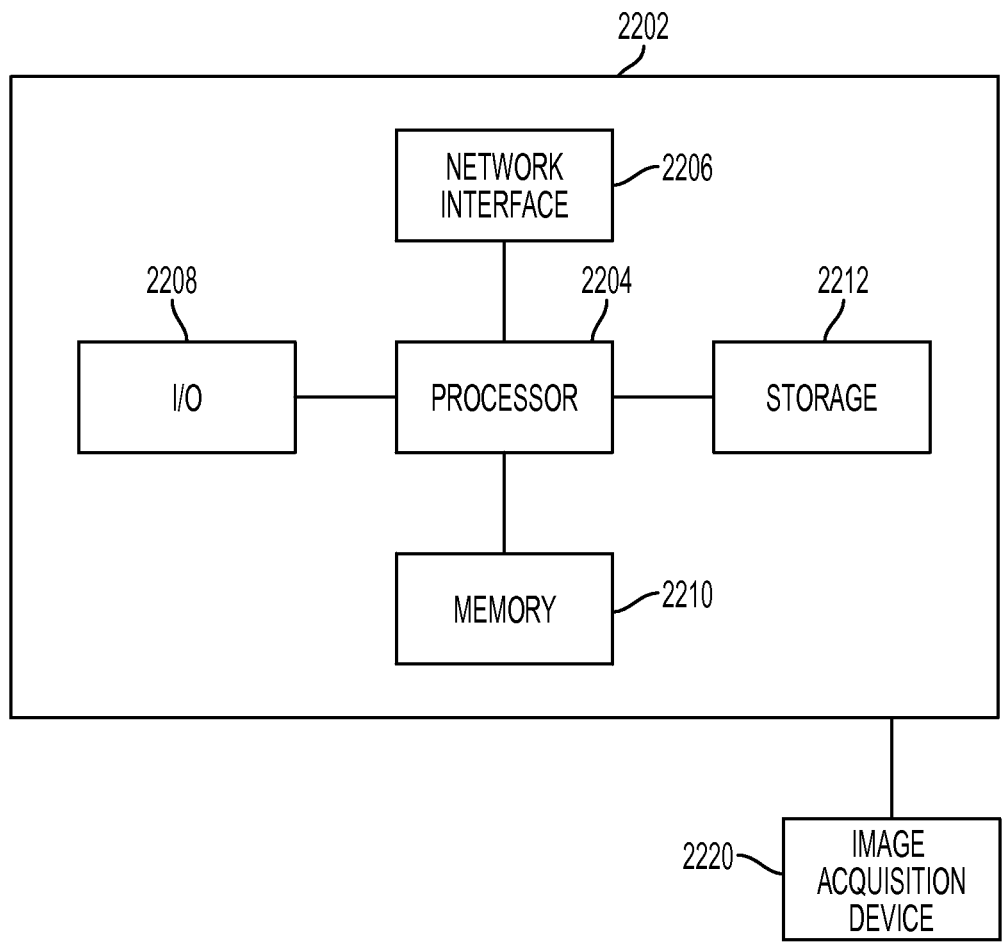
FIG. 22 is a high-level block diagram of a computer capable of implementing the present invention.

The above-described methods for multiple object detection may be implemented on a computer using well-known computer processors, memory units, storage devices, computer software, and other components. A high-level block diagram of such a computer is illustrated in FIG. 22. Computer 2202 contains a processor 2204, which controls the overall operation of the computer 2202 by executing computer program instructions which define such operation. The computer program instructions may be stored in a storage device 2212 (e.g., magnetic disk) and loaded into memory 2210 when execution of the computer program instructions is desired. Thus, the steps of the method of FIGS. 1, 3, and 4 may be defined by the computer program instructions stored in the memory 2210 and/or storage 2212 and controlled by the processor 2204 executing the computer program instructions. An image acquisition device 2220 can be connected to the computer 2202 to input image data to the computer 2202. It is possible to implement the image acquisition device 2220 and the computer 2202 as one device. It is also possible that the image acquisition device 2220 and the computer 2202 communicate wirelessly through a network. The computer 2202 also includes one or more network interfaces 2206 for communicating with other devices via a network. The computer 2202 also includes other input/output devices 2208 that enable user interaction with the computer 2202 (e.g., display, keyboard, mouse, speakers, buttons, etc.). Such input/output devices 2208 may be used in conjunction with a set of computer programs as an annotation tool to annotate volumes received from the image acquisition device 2220. One skilled in the art will recognize that an implementation of an actual computer could contain other components as well, and that FIG. 22 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for detecting multiple objects in an image, comprising:
sequentially detecting a plurality of objects in an image in an order specified by a trained hierarchical detection network, wherein the detection of each object in the image comprises:
obtaining a plurality of sample poses for the object from a proposal distribution of object poses for the object,
weighting each of the plurality of sample poses based on an importance ratio calculated for each sample pose, and
estimating a posterior distribution for the object based on the weighted sample poses.

2. The method of claim 1, wherein the step of obtaining a plurality of sample poses for the object from a proposal distribution of object poses for the object comprises:
determining the proposal distribution for the object based on one or more detected poses for a previously detected one of the plurality of objects.

3. The method of claim 2, wherein the step of determining the proposal distribution for the based one or more detected poses for a previously detected one of the plurality of objects comprises:
applying a Gaussian distribution transition kernel to each of the one or more detected poses of the previously detected one of the plurality of objects, wherein the Gaussian distribution transition kernel is estimated based on training data.

4. The method of claim 1, wherein the step of obtaining a plurality of sample poses for the object from a proposal distribution of object poses for the object comprises:
obtaining the plurality of sample poses using k-means sampling.

5. The method of claim 1, wherein the step of weighting each of the plurality of sample poses based on an importance ratio calculated for each sample comprises:
weighting each of the plurality of sample poses based on an importance ratio calculated for each sample pose using a probability determined for each sample pose by a trained object detector.

6. The method of claim 1, wherein the step of estimating a posterior distribution for the object based on the weighted sample poses comprises:
estimating a posterior distribution for the object and all previously detected ones of the plurality of objects based on the weighted sample poses.

7. The method of claim 6, wherein the step of estimating a posterior distribution for the object and all previously detected ones of the plurality of objects based on the weighted sample poses comprises:
resampling the weighted sample poses using the importance ratios the weighted sample poses to calculate an unweighted approximation of the posterior distribution for the object and all previously detected ones of the plurality of objects.

8. The method of claim 1, wherein the step of estimating a posterior distribution for the object based on the weighted sample poses comprises:
averaging a certain number of highest weighted sample poses.

9. The method of claim 1, wherein the trained hierarchical detection network specifies a hierarchy of scales for detecting the plurality of objects.

10. The method of claim 1, wherein the step of sequentially detecting a plurality of objects in an image in an order specified by a trained hierarchical detection network comprises:

sequentially detecting the plurality of objects in the image in an order specified by the trained hierarchical detection network using Monte Carlo sampling.

11. The method of claim 1, wherein the order for detecting the plurality of objects is one of set automatically in training of the hierarchical detection network, set manually by a user, and set semi-automatically where a partial order is set manually by a user and the remaining order is set automatically in training of the hierarchical detection network.

12. A method of training a hierarchical detection network for detecting a plurality of objects in an image, comprising:
    individually training a plurality of object detectors, each corresponding to one of the plurality of objects, using a first set of annotated training data; and
    automatically determining a detection order for detecting the plurality of objects using a second set of annotated training data and the trained plurality of object detectors.

13. The method of claim 12, wherein the step of automatically determining a detection order for detecting the plurality of objects using a second set of annotated training data and the trained plurality of object detectors comprises:
    selecting a first one of the trained plurality of object detectors to add to a hierarchical detection network, the first one of the trained plurality of object detectors having a highest score for detecting the corresponding one of the plurality of objects in the second set of annotated training data;
    recursively adding a next one of the trained plurality of detectors to connect to a precursor in the hierarchical detection network, by selecting the next one of the trained plurality of detectors and the precursor to maximize an expected value of a score for detecting the corresponding objects in the second set of annotated training data.

14. The method of claim 12, wherein the step of automatically determining a detection order for detecting the plurality of objects using a second set of annotated training data and the trained plurality of object detectors comprises:
    automatically determining a detection order and a scale hierarchy for detecting the plurality of objects.

15. An apparatus for detecting multiple objects in an image, comprising:
    means for sequentially detecting a plurality of objects in an image in an order specified by a trained hierarchical detection network, wherein the means for sequentially detection comprises:
        means for obtaining a plurality of sample poses for an object from a proposal distribution of object poses for the object,
        means for weighting each of the plurality of sample poses based on an importance ratio calculated for each sample pose, and
        means for estimating a posterior distribution for the object based on the weighted sample poses.

16. The apparatus of claim 15, wherein the means for obtaining a plurality of sample poses for the object from a proposal distribution of object poses for the object comprises:
    means for determining the proposal distribution for the object based on one or more detected poses for a previously detected one of the plurality of objects.

17. The apparatus of claim 16, wherein the means for determining the proposal distribution for the based one or more detected poses for a previously detected one of the plurality of objects comprises:
    means for applying a Gaussian distribution transition kernel to each of the one or more detected poses of the previously detected one of the plurality of objects, wherein the Gaussian distribution transition kernel is estimated based on training data.

18. The apparatus of claim 15, wherein the means for weighting each of the plurality of sample poses based on an importance ratio calculated for each sample comprises:
    means for weighting each of the plurality of sample poses based on an importance ratio calculated for each sample pose using a probability determined for each sample pose by a trained object detector.

19. The apparatus of claim 15, wherein the means for estimating a posterior distribution for the object based on the weighted sample poses comprises:
    means for estimating a posterior distribution for the object and all previously detected ones of the plurality of objects based on the weighted sample poses.

20. The apparatus of claim 19, wherein the means for estimating a posterior distribution for the object and all previously detected ones of the plurality of objects based on the weighted sample poses comprises:
    means for resampling the weighted sample poses using the importance ratios the weighted sample poses to calculate an unweighted approximation of the posterior distribution for the object and all previously detected ones of the plurality of objects.

21. The apparatus of claim 15, wherein the trained hierarchical detection network specifies a hierarchy of scales for detecting the plurality of objects.

22. An apparatus for training a hierarchical detection network for detecting a plurality of objects in an image, comprising:
    means for individually training a plurality of object detectors, each corresponding to one of the plurality of objects, using a first set of annotated training data; and
    means for automatically determining a detection order for detecting the plurality of objects using a second set of annotated training data and the trained plurality of object detectors.

23. The apparatus of claim 22, wherein the means for automatically determining a detection order for detecting the plurality of objects using a second set of annotated training data and the trained plurality of object detectors comprises:
    means for selecting a first one of the trained plurality of object detectors to add to a hierarchical detection network, the first one of the trained plurality of object detectors having a highest score for detecting the corresponding one of the plurality of objects in the second set of annotated training data;
    means for recursively adding a next one of the trained plurality of detectors to connect to a precursor in the hierarchical detection network, by selecting the next one of the trained plurality of detectors and the precursor to maximize an expected value of a score for detecting the corresponding objects in the second set of annotated training data.

24. The apparatus of claim 22, wherein the means for automatically determining a detection order for detecting the plurality of objects using a second set of annotated training data and the trained plurality of object detectors comprises:
    means for automatically determining a detection order and a scale hierarchy for detecting the plurality of objects.

25. A non-transitory computer readable medium encoded with computer executable instructions for detecting multiple objects in an image, the computer executable instructions defining steps comprising:

sequentially detecting a plurality of objects in an image in an order specified by a trained hierarchical detection network, wherein the detection of each object in the image comprises:
obtaining a plurality of sample poses for the object from a proposal distribution of object poses for the object,
weighting each of the plurality of sample poses based on an importance ratio calculated for each sample pose, and
estimating a posterior distribution for the object based on the weighted sample poses.

26. The computer readable medium of claim 25, wherein the computer executable instructions defining the step of obtaining a plurality of sample poses for the object from a proposal distribution of object poses for the object comprise computer executable instructions defining the step of:
determining the proposal distribution for the object based on one or more detected poses for a previously detected one of the plurality of objects.

27. The computer readable medium of claim 26, wherein the computer executable instructions defining the step of determining the proposal distribution for the based one or more detected poses for a previously detected one of the plurality of objects comprise computer executable instructions defining the step of:
applying a Gaussian distribution transition kernel to each of the one or more detected poses of the previously detected one of the plurality of objects, wherein the Gaussian distribution transition kernel is estimated based on training data.

28. The computer readable medium of claim 25, wherein the computer executable instructions defining the step of weighting each of the plurality of sample poses based on an importance ratio calculated for each sample comprise computer executable instructions defining the step of:
weighting each of the plurality of sample poses based on an importance ratio calculated for each sample pose using a probability determined for each sample pose by a trained object detector.

29. The computer readable medium of claim 25, wherein the computer executable instructions defining the step of estimating a posterior distribution for the object based on the weighted sample poses comprise computer executable instructions defining the step of:
estimating a posterior distribution for the object and all previously detected ones of the plurality of objects based on the weighted sample poses.

30. The computer readable medium of claim 29, wherein the computer executable instructions defining the step of estimating a posterior distribution for the object and all previously detected ones of the plurality of objects based on the weighted sample poses comprise computer executable instructions defining the step of:
resampling the weighted sample poses using the importance ratios the weighted sample poses to calculate an unweighted approximation of the posterior distribution for the object and all previously detected ones of the plurality of objects.

31. The computer readable medium of claim 25, wherein the trained hierarchical detection network specifies a hierarchy of scales for detecting the plurality of objects.

32. A non-transitory computer readable medium encoded with computer executable instructions for training a hierarchical detection network for detecting a plurality of objects in an image, the computer executable instructions defining steps comprising:
individually training a plurality of object detectors, each corresponding to one of the plurality of objects, using a first set of annotated training data; and
automatically determining a detection order for detecting the plurality of objects using a second set of annotated training data and the trained plurality of object detectors.

33. The computer readable medium of claim 32, wherein the computer executable instructions defining the step of automatically determining a detection order for detecting the plurality of objects using a second set of annotated training data and the trained plurality of object detectors comprise computer executable instructions defining the steps of:
selecting a first one of the trained plurality of object detectors to add to a hierarchical detection network, the first one of the trained plurality of object detectors having a highest score for detecting the corresponding one of the plurality of objects in the second set of annotated training data;
recursively adding a next one of the trained plurality of detectors to connect to a precursor in the hierarchical detection network, by selecting the next one of the trained plurality of detectors and the precursor to maximize an expected value of a score for detecting the corresponding objects in the second set of annotated training data.

34. The computer readable medium of claim 32, wherein the computer executable instructions defining the step of automatically determining a detection order for detecting the plurality of objects using a second set of annotated training data and the trained plurality of object detectors comprise computer executable instructions defining the step of:
automatically determining a detection order and a scale hierarchy for detecting the plurality of objects.

* * * * *